United States Patent [19]

Boray et al.

[11] 4,428,957
[45] Jan. 31, 1984

[54] 6-ISOTHIOCYANO-5-METHOXY-2-TERT.-BUTYLBENZTHIAZOLE AND A METHOD OF CONTROLLING RUMINANT LIVER FLUKES THEREWITH

[75] Inventors: Joseph C. Boray, Neutral Bay, Australia; Jean J. Gallay, Blumenrain; Gedeon Sarasin, Basel, both of Switzerland

[73] Assignee: Ciba-Geigy Corporation, Ardsley, N.Y.

[21] Appl. No.: 260,651

[22] Filed: May 4, 1981

Related U.S. Application Data

[63] Continuation-in-part of Ser. No. 59,087, Jul. 19, 1979, abandoned.

[30] Foreign Application Priority Data

Jul. 27, 1978 [CH] Switzerland .......................... 8082/78

[51] Int. Cl.³ .................. A61K 31/425; C07D 277/64
[52] U.S. Cl. ...................................... 424/270; 548/178
[58] Field of Search .......................... 548/178; 424/270

[56] References Cited

FOREIGN PATENT DOCUMENTS 565164  6/1975  Switzerland ..................... 548/178
566321  7/1975  Switzerland ..................... 548/178
585214  1/1977  Switzerland ..................... 548/178
587837  3/1977  Switzerland ..................... 548/178

Primary Examiner—Paul M. Coughlan, Jr.
Assistant Examiner—D. B. Springer
Attorney, Agent, or Firm—Frederick H. Rabin

[57] ABSTRACT

The isothiocyanobenzothiazole derivative of the formula

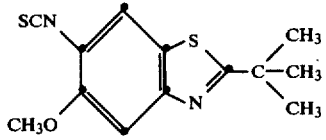

and also salts thereof nontoxic to warm-blooded animals have, besides generally good anthelmintic properties, especially a particularly pronounced action against filariasis, schistosomiasis and gastrointestinal helminths in warm-blooded organisms and equally against liver flukes in sheep. The active substance, together with suitable carriers and additives, is administered perorally or via the abomasum, in the form of solutions, emulsions, suspensions, powders, tablets, boluses and capsules.

6 Claims, No Drawings

6-ISOTHIOCYANO-5-METHOXY-2-TERT.-BUTYL-BENZTHIAZOLE AND A METHOD OF CONTROLLING RUMINANT LIVER FLUKES THEREWITH

This is a continuation-in-part of our co-pending application Ser. No. 59,087, filed July 19, 1979 now abandoned.

The present invention relates to the isothiocyanobenzothiazole derivative of the formula I

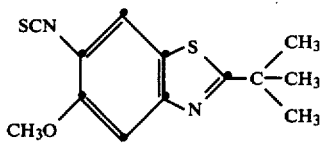

including salts thereof nontoxic to warm-blooded organisms; to compositions containing this compound, or such a salt thereof, as active substance; and to the use of this compound, or of such a salt thereof, for combatting parasitic helminths, especially for combatting filariasis, schistosominasis and gastro-intestinal helminths in warm-blooded organisms and equally for the control of liver flukes (Fasciola hepatica) in sheep.

In the Swiss Patent Application Nos. 566,321 and 565,164 and also Nos. 585,214 and 587,837, there are already described groups of isothiocyanobenzothiazoles, in which the compound of the formula I according to the invention is generically embraced but is not specifically disclosed as a separate compound.

It is suggested in the two firstly stated patent specifications that these isothiocyanobenzothiazoles be used for controlling helminths in productive animals, with the term "helminths" covering nematodes, cestodes and trematodes. In the specification of these patents, verification is provided of the effectiveness of some of the disclosed compounds against certain of the mentioned parasites purely in laboratory animals such as rats and mice, with however one exception. The exception concerns the control of *Ascaridia galli* in fowl. Test results given by compounds mentioned in express terms with respect to their effectiveness against liver flukes (*Fasciola hepatica*) relate however exclusively to the laboratory animal (rat) as host organism.

The two last-mentioned patent specifications specify for one group of these isothiocyanobenzothiazoles, in addition to the broad anthelmintic field of activity attributed to the compounds embraced, a special field of application, namely the control of the nematodes, Oesophagostomum columbianum, with which the distal intestinal region may be infested.

The occurrence of the dangerous and widely spread Fasciolosis leads to inhibited growth, to reduced output and even to cases of death of the infested animals, and hence to great damage and losses in yield, particularly in sheep breeding. The task of combatting and preventing Fasciolosis in sheep is therefore urgent, so as to avoid above all such economically serious losses in animal production.

On account of the wide spectrum of parasites embraced by the term "helminths", it has not hitherto been possible, in spite of numerous preparations in the field of helminth control, to develop an active substance which has, besides a good action against nematodes and cestodes, at the same time an excellent action against liver flukes in sheep, and which can therefore ensure a successful control of Fasciolosis. It has moreover been shown that the agents so far suggested for combating liver flukes frequently produce considerable toxic secondary effects, a factor which in any case sets narrow limits to the application of these agents by virtue of their unfavourable therapeutic index.

Thus, also with respect to the compounds which are specifically disclosed in the four patent specifications mentioned and which are structurally similar to the compound of the formula I, no evidence could be provided of a possible usefulness of these compounds in the field of the control of liver flukes in the productive animal, for example in sheep, in practice, although the results obtained with laboratory animals were promising.

It is therefore to be considered especially surprising that a particular compound among those embraced in general in the stated specifications, which compound however is not specifically disclosed, namely the compound of the formula I according to the invention, exhibits, besides having generally good anthelmintic properties, an excellent action against liver flukes in sheep. Furthermore, the compound according to the invention has an extraordinarily favourable therapeutic index (maximum tolerated dose/minimum effective dose) of about 13, and is hence particularly suitable for treatments on a broad basis and at all stages of age of the sheep.

Furthermore, the compound of the formula I according to the present invention and non-toxic salts thereof have surprisingly been found to exhibit extremely potent anthelminthic activities against a broad variety of parasitic helminths, especially Nematodes and Trematodes, in warm-blooded organisms.

In various test models an excellent activity against filariasis, schistosomiasis and gastro-intestinal helminths has been ascertained. The pronounced potency against filariasis, micro- and macrofilariae, has been assessed, e.g., against *Litomosoides carinii*, *Dipetalonea viteae* (each in Mongolian jirds and multimammate rats), *Brugia pahangi* and *Brugia malayi* (each in multimammate rats). Experiments with *Schistosoma mansoni* (in mice and Syrian hamsters) and *Schistosoma japonicum* (in dogs) exhibit pronounced antischistosomal effects. Furthermore, according to tests with various Nipprostrongylus species the inventive compound and its non-toxic salts have been found to display surprising properties against gastro-intestinal helminths.

Accordingly, the compound of the formula I and its non-toxic salts are usefull in combatting filariasis, schistosominasis and gastro-intestinal helminths and as medicaments for the treatment of helminthic infections.

Suitable salts of the isothiocyanobenzothiazole of the formula I, which are nontoxic to warm-blooded organisms, are addition compounds with inorganic or organic acids, preferably fairly strong acids. Examples are: hydrochloric acid, hydrobromic acid, sulfuric acid, phosphoric acid, acetic acid, adipic acid, maleic acid, tartaric acid, lactic acid, citric acid, glutamic acid, aconitic acid, sulfamic acid, methanesulfonic acid and p-toluenesulfonic acid.

The active substance according to the invention can be administered in single in repeated doses, the single doses being, depending on the species of the animals, preferably between 5 and 100 mg per kg of body weight.

In veterinary application a better effect can often be obtained in some cases by a protracted administration of the active substance, or smaller complete doses may be sufficient. The active substance of the invention and mixtures containing the active substance can also be added to the feed. The finished feed contains the active substance of the formula I preferably at a concentration of about 0.05 to 1 percent by weitht. The novel active substance can be administered to the animals, perorally or via the abomasum, in the form of solutions, emulsions, suspensions (drenches), powders, tablets, boluses and capsules. These preparations are obtained by using, for example, customary solid carriers, such as kaolin, talc, bentonite, sodium chloride, calcium phosphate, carbohydrate, cellulose powder, cottonseed meal, carbowaxes or gelatine, or liquids such as water, optionally with the addition of surface-active substances, such as ionic or nonionic dispersing agents, and also oils and other solvents and diluents harmless to the animal organism. With application of the active substance in anthelmintic compositions in the form of feed concentrates, the carriers used can be for example: production feed, fodder grain or protein concentrates.

Other biocidal active substances, for example pesticides, can be added to the described compositions according to the invention. The compositions can thus contain, besides the stated compound of the formula I, for example fungicides, bactericides, fungistatics, bacteriostatics and ectoparasiticides, or other active substances for widening the spectrum of activity.

The compound of the formula I and its non-toxic salts are preferably used in the form of pharmaceutical compositions applicable to warm-blooded organisms.

The Pharmaceutical compositions according to the invention which contain a compound of the formula I are those which are intended for enteral, such as oral, rectal or parenteral administration on warm-blooded organisms and which contain the pharmacological active compound on its own or together with an excipient which can be used pharmaceutically.

The new pharmaceutical compositions contain from about 10% up to about 95%, and preferably from about 20% up to about 90%, of the active compound. Pharmaceutical compositions according to the invention are, for example, those in the form of elixirs or in the form of dosage units, such as dragées, tablets, capsules, suppositories or ampoules. The solid compositions contain per dosage unit form from about 0,1 g to about 1,5 g, preferably from about 0,25 g to about 1 g of the active ingredient, whereas liquid compositions contain from about 0.5% to about 15% active ingredient.

The pharmaceutical compositions of the present invention are manufactured in a manner which is in itself known, for example by means of conventional mixing, granulating, dragée-making, dissolving or lyophilising processes.

Compositions for oral use can be obtained, for example, by combining the active compound with solid excipients, optionally granulating a resulting mixture and processing the mixture or granules, after adding suitable auxiliaries if desired or necessary, to give tablets or dragee cores. Suitable excipients are, in particular, fillers, such as sugars, for example lactose or sucrose, mannitol or sorbitol, cellulose formulations and/or calcium phosphates, for example tricalcium phosphate or calcium hydrogen phosphate, as well as binders, such as starch pastes using, for example, maize starch, wheat starch, rice starch or potato starch, gelatine, tragacanth, methylcellulose, hydroxypropyl-methylcellulose, sodium carboxymethylcellulose and/or polyvinylpyrrolidone, and/or, if desired, disintegrating agents, such as the abovementioned starches, and also carboxymethylstarch, crosslinked polyvinylpyrrolidone, agar or alginic acid or a salt thereof, such as sodium alginate. Auxiliaries are, above all, flow-regulating agents and lubricants, for example silica, talc, stearic acid or salts thereof, such as magnesium stearate or calcium stearate, and/or polyethylene glycol. Dragée cores are provided with suitable coatings which, if desired, are resistant to gastric juices, and for this purpose, inter alia, concentrated sugar solutions, which optionally contain gum arabic, talc, polyvinylpyrrolidone, polyethylene glycol and/or titanium dioxide, lacquer solutions in suitable organic solvents or solvent mixtures or, in order to produce coatings resistant to gastric juices, solutions of suitable cellulose formulations, such as acetylcellulose phthalate or hydroxypropylmethylcellulose phthalate, are used. Dyestuffs or pigments can be added to the tablets or dragée coatings, for example for identification or in order to characterise different doses of active compound.

Other pharmaceutical compositions which can be used orally are push-fit capsules made of gelatine, as well as soft, sealed capsules made of gelatine and a plasticiser, such as glycerol or sorbitol. The push-fit capsules can contain the active compound in the form of granules, for example mixed with fillers, such as lactose, binders, such as starches, and/or lubricants, such as talc or magnesium stearate, and, optionally, stabilisers. In soft capsules, the active compound is preferably dissolved or suspended in suitable liquids, such as fatty oils, liquid paraffin or liquid polyethylene glycols, it also being possible to add stabilisers.

Possible pharmaceutical composition which can be used rectally are, for example, suppositories, which consist of a combination of the active compound with a suppository base. Suitable suppository bases are, for example, natural or synthetic triglycerides, paraffin hydrocarbons, polyethylene glycols or higher alkanols. In addition, it is also possible to use gelatine rectal capsules which consist of a combination of the active compound and a base; bases which can be used are, for example, liquid triglycerides, polyethylene glycols or paraffin hydrocarbons.

Suitable compositions for parenteral administration are, above all, aqueous solutions of an active compound in a water-soluble form, for example of a water-soluble salt, and also suspensions of the active compound, such as corresponding oily injection suspensions, for which suitable lipophilic solvents or vehicles, such as fatty oils, for example sesame oil, or synthetic fatty acid esters, for example ethyl oleate or triglycerides, are used, or aqueous injection suspensions which contain substances which increase the viscosity, for example sodium carboxymethylcellulose, sorbitol and/or dextran, and optionally also contain stabilisers.

It is a further object of the present invention to provide a method of combatting parasitic helminths in warm-blooded organisms, which method comprises administering the new compound of the formula I and its non-toxic salts. In this method, the above pharmaceutical compositions are used in particular for oral administration. In general, 1 to about 10 single dose units are sufficient for a successful therapy, depending on the species of warm-blooded organism, on age and the state of health of the individual and on the mode of administration. For example, to a warm-blooded organism of about 70 kg body weight a daily dose from about 0.25 g to about 1.5 g, preferably from about 0.5 to about 1.0 g, of the active ingredient is administered.

The isothiocyanobenzothiazole of the formula I can be produced using known processes, such as are described for example in the Swiss Patent Application No. 566,321, by reacting the aminobenzothiazole of the formula II

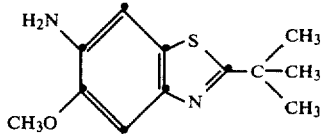

with a thiocarbonic acid derivative of the formula

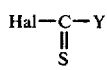

in which "Hal" is chlorine or bromine, and Y is chlorine, bromine or a dialkylamino group, in an inert solvent or diluent, at temperatures of $-20°$ to $+100°$ C., preferably $-10°$ to $+30°$ C.

EXAMPLE 1

Production of 6-isothiocyano-5-methoxy-2-tert.-butyl-benzothiazole 32.0 g of 6-amino-5-methoxy-2-tert.-butyl-benzothiazole is dissolved in 200 ml of dioxane, and the solution is stirred at $10°-15°$ C.; a mixture of 25 ml of thiophosgene and 25 ml of dioxane is added dropwise with stirring, and the reaction mixture is stirred at the same temperature for a further 18 hours; it is then diluted to 400 ml with water and stirred for one further hour. The precipitate which has formed is filtered off with suction; it is subsequently washed with water and dissolved moist in 500 ml of hot acetonitrile; it is then diluted with 100 ml of water and cooled. The product which has crystallised out is filtered off with suction and dried to yield f.e. 18 to 25 g of 6-isothiocyano-5-methoxy-2-tert.-butyl-benzothiazole having a melting point of $73°-74°$ C.

EXAMPLE 2

Tablets containing 0,5 g of 6-isothiocyano-5-methoxy-2-tert.-butyl-benzthiazole can be prepared as follows:

| Composition (for 10,000 tablets) | |
|---|---|
| 6-Isothiocyano-5-methoxy-2-tert.-butyl-benzthiazole | 5000 g |
| corn starch | 790 g |
| stearic acid | 30 g |
| magnesium stearate | 30 g |
| talc | 400 g |
| water | q.s. |

A mixture of the 6-Isothiocyano-5-methoxy-2-tert.-butyl-benzthiazole and 500 g of corn starch is made into a paste with about 1300 ml of demineralised water and uniformly moistened with a further 600 g of demineralised water. The mixture is kneaded to a slightly plastic mass, which is forced through a sieve having a mesh size of about 3 mm. The granulate thereby obtained is then dried and sieved. The dry granulate, which is brought to a uniform particle size, is mixed with the magnesium stearate, stearic acid, talc and 290 g of corn starch, and the mixture is compressed to tablets of 0.625 g.

Tablets containing 0,5 g can be prepared in analogous manner.

The anthelmintic activity is demonstrated by means of the following tests:

1. Test on sheep infected with nematodes such as *Haemonchus contortus* and *Trichostrongylus colubriformis*

The active substance is introduced in the form of a suspension by means of a stomach probe, or by injection, into the rumen of sheep which have been artificially infested with nematodes such as *Haemonchus controtus* and *Trichostrongylus colubriformis*. Three animals are used per test and per dose, each sheep being treated with just one single dose. An initial evaluation is made by comparing the numbers of worm eggs excreted in the dropping of the sheep before and after the treatment. Seven to ten days after the treatment, the sheep are killed and dissected. A second evaluation is then made by carrying out a count of the worm which have remained behind in the intestine after the treatment. Sheep which have been simultaneously and similarly infested but not treated with the active substance are used as a control or comparison.

2. Test on sheep infested with cestodes such as *Moniezia benedeni*

The active substance is introduced in the form of a suspension, by means of a stomach probe or by injection, into the rumen of sheep which are infested with cestodes such as *Moniezia benedeni*. Three animals are used per test and per dose, each sheep being treated with just one single dose. The sheep are killed and dissected seven to ten days after the treatment. The evaluation is made on the basis of a count of the worms which have remained behind in the intestine after the treatment. Sheep which have been simultaneously and similarly infested but not treated with the active substance are used as a control or comparison.

3. Test on sheep infested with *Fasciola hepatica*

The active substance is introduced in the form of a suspension, by means of a stomach probe or by injection, into the rumen of sheep which have been artificially infested with *Fasciola hepatica*. Three animals are used per test and per dose, each animal being treated with just one single dose. An initial evaluation is made by comparing the numbers of worm eggs excreted in the droppings of the sheep before and after the treatment. The sheep are killed and dissected three to four weeks after the treatment. The second evaluation is on the basis of a count of the liver flukes which have remained behind in the hepatic ducts after the treatment. Simultaneously and similarly infested but untreated sheep are used as a control or comparison. The difference in the numbers of liver flukes in the two groups is a measure of the degree of effectiveness of the active substance tested.

The compatibility is demonstrated by means of the following tests.

Compatibility in the case of the sheep

The active substances are introduced in the form of a suspension, by means of a stomach probe or by injection, into the rumen of the experimental animals. Three to five sheep are used per test and per dose, each animal being treated with just one single dose. The sheep are kept under observation during 14 days after the treatment, and they are weighed at regular intervals. Any clinical symptoms and cases of death occurring are recorded during this period. Similar sheep (with regard to breed, age and weight) which have not been treated with the respective active substance are kept as control animals together with the treated experimental animals. The same parameters are recorded in the case of the control sheep as in the case of the treated sheep. The minimum effective dose (MED) of 25 mg/kg (see Table) in the case of the compound of formula I is effective in sheep not only against *Fasciola hepatica* but also against nematodes such as *Haemonchus concortus*, *Trichostrongylus colubriformis* and *Ostertagia circumcincta*, and against cestodes such as *Moniezia benedeni*.

Test results (treatment of *Fasciola hepafica* infestation of sheep)

| No. | Compound | MED* mg/kg body weight | MTD* mg/kg body weight |
|---|---|---|---|
| 1 | [SCN-, CH3O- substituted benzothiazole with C(CH3)3 group] | 25 | 320 |
| 2+ | [SCN- substituted benzothiazole with C(CH3)3 group] | 100 | 200 |
| 3+ | [SCN-, CH3O- substituted benzothiazole with CH(CH3)2 group] | >100 | 200 |
| 4+ | [SCN- substituted benzothiazole with CH(CH3)2 group] | >200 | 200 |

*MED = minimum effective dose
*MTD = maximum tolerated dose
+from Swiss Patent No. 565,164

What is claimed is:
1. A compound of the formula I

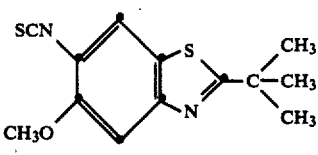

(I)

and pharmaceutically acceptable salts thereof.

2. A composition for combatting liver flukes in warm-blooded organisms comprising as an active ingredient an anthelminthically effective amount of the compound of the formula I according to claim 1 together with suitable carriers and/or auxiliaries.

3. A composition according to claim 2 in which the dosage unit forms are dragees, tablets or capsules.

4. A composition according to claim 2 containing from about 0,25 g to about 1,5 g of the active ingredient.

5. A method for the control of liver flukes comprising administering to ruminants infested therewith an anthelminthically effective amount of the compound of the formula I according to claim 1.

6. A method according claim 5 in which the ruminants are sheep.